United States Patent
Jeon et al.

(10) Patent No.: US 11,745,025 B2
(45) Date of Patent: Sep. 5, 2023

(54) DEEP BODY SPREAD MICROWAVE HYPERTHERMIA DEVICE FOR PERSONAL USES AND OPERATING METHOD THEREOF

(71) Applicant: Electronics and Telecommunications Research Institute, Daejeon (KR)

(72) Inventors: Soon Ik Jeon, Sejong-si (KR); Bo Ra Kim, Sejong-si (KR); Jang Yeol Kim, Daejeon (KR); Seong-Ho Son, Daejeon (KR); Kwang Jae Lee, Daejeon (KR); Soo-Ho Sohn, Daejeon (KR); Ho Jin Lee, Daejeon (KR)

(73) Assignee: Electronics and Telecommunications Research Institute, Daejeon (KR)

( * ) Notice: Subject to any disclaimer, the term of this patent is extended or adjusted under 35 U.S.C. 154(b) by 903 days.

(21) Appl. No.: 16/670,729

(22) Filed: Oct. 31, 2019

(65) Prior Publication Data

US 2020/0139150 A1    May 7, 2020

(30) Foreign Application Priority Data

Nov. 7, 2018 (KR) .......................... 10-2018-0135966
Jul. 3, 2019 (KR) .......................... 10-2019-0080174

(51) Int. Cl.
*A61N 5/02* (2006.01)
*A61F 7/00* (2006.01)

(52) U.S. Cl.
CPC ................ *A61N 5/025* (2013.01); *A61F 7/00* (2013.01); *A61F 2007/0088* (2013.01)

(58) Field of Classification Search
CPC .... A61F 2007/0088; A61F 7/00; A61N 5/025
See application file for complete search history.

(56) References Cited

U.S. PATENT DOCUMENTS

| 6,470,217 B1 | 10/2002 | Fenn et al. |
| 2006/0132375 A1 | 6/2006 | Kim et al. |
| 2010/0036369 A1* | 2/2010 | Hancock ............ A61B 18/1815 606/33 |
| 2015/0313499 A1 | 11/2015 | Sohn |
| 2019/0111275 A1* | 4/2019 | Jeon ...................... H01Q 1/273 |

FOREIGN PATENT DOCUMENTS

| JP | 2015119798 A | 7/2015 |
| JP | 2017518788 A | 7/2017 |
| KR | 101475400 B1 | 1/2015 |

\* cited by examiner

*Primary Examiner* — Lynsey C Eiseman
*Assistant Examiner* — Amanda L Steinberg
(74) *Attorney, Agent, or Firm* — William Park & Associates Ltd.

(57) ABSTRACT

Disclosed are a deep body spread microwave hyperthermia device for personal uses and an operation method thereof. The operating method may include generating a control signal to control patches attached to the skin of a user, dividing the control signal into a first signal and a second signal having a phase different from a phase of the first signal, transmitting the first signal and the second signal to patches attached to different positions, among the patches, and producing hyperthermia in a body of the user by radiating radio waves based on the first signal or the second signal received by each of the patches.

12 Claims, 18 Drawing Sheets

FIG. 5B

|  | First phase | Second phase |
|---|---|---|
| Channel 1 | Ø1 signal | Ø1 signal |
| Channel 2 | Ø1 signal | Ø2 signal |
| Channel 3 | Ø2 signal | Ø2 signal |
| Channel 4 | Ø2 signal | Ø1 signal |

802

803

1002

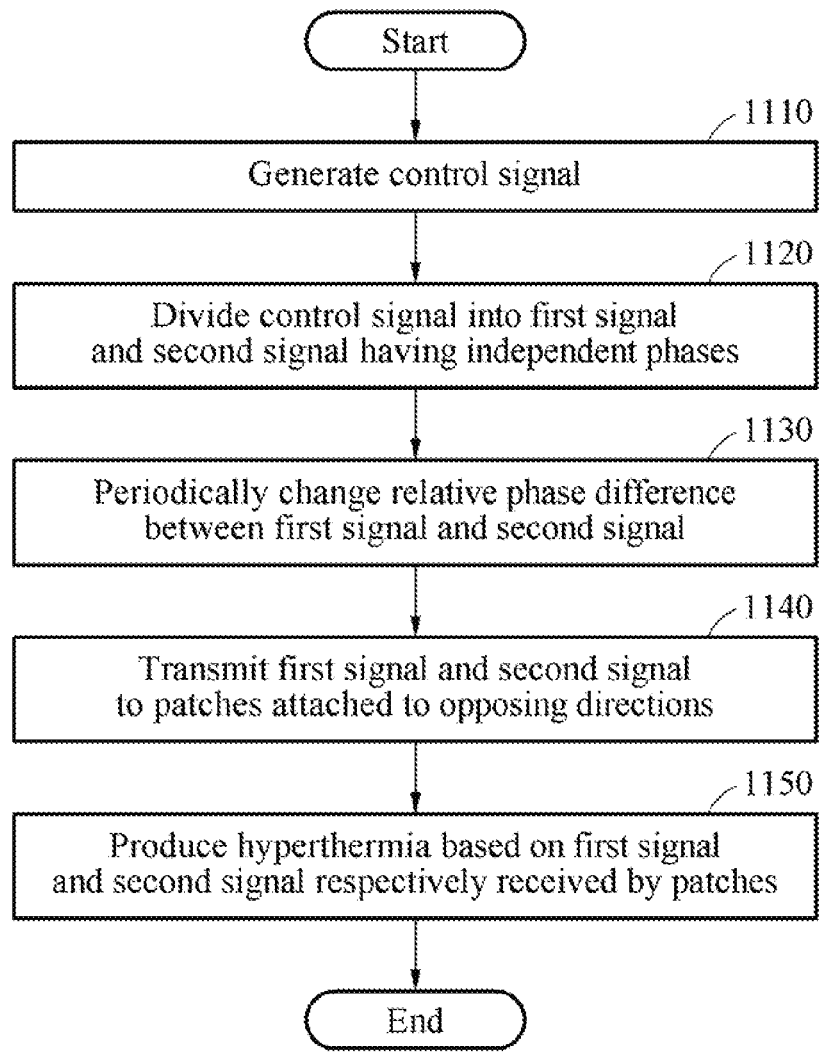

DEEP BODY SPREAD MICROWAVE HYPERTHERMIA DEVICE FOR PERSONAL USES AND OPERATING METHOD THEREOF

CROSS-REFERENCE TO RELATED APPLICATION(S)

This application claims the priority benefit of Korean Patent Application No. 10-2018-0135966 filed on Nov. 7, 2018, and Korean Patent Application No. 10-2019-0080174 filed on Jul. 3, 2019, in the Korean Intellectual Property Office, the disclosures of which are incorporated herein by reference for all purposes.

BACKGROUND

1. Field of the Invention

One or more example embodiments relate to a deep body spread microwave hyperthermia device for personal uses, and more particularly, to a device and method for moving a position of a hyperthermia region formed in a body of a user using microwaves radiated at different positions.

This work was supported by the National Research Council of Science & Technology (NST) grant by the Korea government.

2. Description of the Related Art

A microwave hyperthermia therapy device is a device for treating cancer occurring at a site of breast tissue, in detail, a device which treats cancer by exposing the cancer of breast tissue and the site of cancer to higher temperatures.

An existing microwave hyperthermia therapy device divides microwave signals into two directions, controls phases of the two microwaves, and supplies signals to two waveguide antennas placed on the left and right sides of a breast by adjusting microwave power. The existing microwave hyperthermia therapy device propagates the signals to the breast compressed with compression plates using the waveguide antennas, and intensively produces heat at one region in the human body by controlling phases and intensities, without producing heat in the other regions, and cools unnecessary heat by blowing air.

However, the existing microwave hyperthermia therapy device is a device designed for treating cancer and lesions of breast tissue by producing hyperthermia at only one site using microwaves, and thus may produce hyperthermia at a predetermined position, but may not apply the hyperthermia to an entire predetermined region.

In addition, the existing microwave hyperthermia therapy device requires an electric field probe and a temperature probe sensor to be inserted into a human body to monitor radio waves and the temperature, and an element to cool the heat occurring on the skin with a blowing device, and thus the complexity of the device is high and incurs expenses, and a user is forced to accept an insertion of sensor.

Accordingly, there is a desire for a method of performing hyperthermia therapy by producing hyperthermia in the entirety of a predetermined region of a body of a user with a relatively simple structure, when compared to the existing microwave hyperthermia therapy device.

SUMMARY

An aspect provides a device and method that may move a position at which hyperthermia is produced by patches, by shifting a phase of a first signal and a phase of a second signal to increase a phase difference between the first signal and the second signal over time.

Another aspect also provides a device and method that may produce hyperthermia in a region in which hyperthermia is not produced by patches, by changing types of signals to be transmitted to the patches.

According to an aspect, there is provided an operating method of a deep body spread hyperthermia device, the operating method including generating a control signal to control patches attached to the skin of a user, dividing the control signal into a first signal and a second signal having a phase different from a phase of the first signal, transmitting the first signal and the second signal to patches attached to different positions, among the patches, and producing hyperthermia in a body of the user by radiating radio waves based on the first signal or the second signal received by each of the patches.

The operating method may further include shifting a phase of the first signal and a phase of the second signal to increase a phase difference between the first signal and the second signal over time, wherein the transmitting may include transmitting the phase-shifted first signal and the phase-shifted second signal to patches attached to different positions, among the patches.

The shifting may include increasing the phase difference between the first signal and the second signal 360 degrees at time intervals.

The shifting may include repeating increasing the phase difference between the first signal and the second signal from 0 degrees to 360 degrees at a first time interval, and decreasing the phase difference between the first signal and the second signal from 360 degrees to 0 degrees at a second time interval following the first time interval.

The transmitting may include changing signals to be transmitted to the patches from the first signal to the second signal or from the second signal to the first signal to change a position of hyperthermia to be produced in the body of the user.

The patches may include a first patch, a second patch, a third patch attached to an opposing direction of the first patch, and a fourth patch attached to an opposing direction of the second patch based on the body of the user, and the transmitting may include transmitting the first signal and the second signal to the first patch and the third patch, respectively, and transmitting the first signal or the second signal to the second patch and the fourth patch depending on a phase.

The transmitting may include transmitting the first signal to the second patch and the second signal to the fourth patch in a first phase, and transmitting the second signal to the second patch and the first signal to the fourth patch in a second phase.

According to another aspect, there is provided a deep body spread hyperthermia device including a plurality of patches to be attached to the skin of a user to produce hyperthermia in a body of the user by radiating radio waves into the body of the user, and a signal processor configured to generate a first signal and a second signal having a phase different from a phase of the first signal to control the patches to radiate the radio waves, and transmit the first signal and the second signal to the patches, wherein the signal processor may be configured to transmit the first signal and the second signal respectively to patches attached to opposing directions, among the patches.

The signal processor may be configured to shift a phase of the first signal and a phase of the second signal to increase a phase difference between the first signal and the second signal over time.

The signal processor may be configured to increase the phase difference between the first signal and the second signal 360 degrees at time intervals.

The signal processor may be configured to repeat increasing the phase difference between the first signal and the second signal from 0 degrees to 360 degrees at a first time interval, and decreasing the phase difference between the first signal and the second signal from 360 degrees to 0 degrees at a second time interval following the first time interval.

The signal processor may be configured to change signals to be transmitted to the patches from the first signal to the second signal or from the second signal to the first signal to change a position of hyperthermia to be produced in the body of the user.

The patches may include a first patch configured to receive the first signal at all times, a second patch configured to receive the first signal in a first phase and receive the second signal in a second phase, a third patch to be attached to an opposing direction of the first patch based on the body of the user, the third patch configured to receive the second signal at all times, and a fourth patch to be attached to an opposing direction of the second patch based on the body of the user, the fourth patch configured to receive the second signal in the first phase and receive the first signal in the second phase.

The signal processor may be configured to transmit the first signal to the second patch and the second signal to the fourth patch in the first phase, and transmit the second signal to the second patch and the first signal to the fourth patch in the second phase.

Additional aspects of example embodiments will be set forth in part in the description which follows and, in part, will be apparent from the description, or may be learned by practice of the disclosure.

BRIEF DESCRIPTION OF THE DRAWINGS

These and/or other aspects, features, and advantages of the invention will become apparent and more readily appreciated from the following description of example embodiments, taken in conjunction with the accompanying drawings of which:

FIGS. 5A and 5B illustrate an example of a phase selection matrix circuit included in a signal processor according to an example embodiment;

FIG. 11 is a flowchart illustrating a deep body spread method according to an example embodiment.

DETAILED DESCRIPTION

Figure 1:
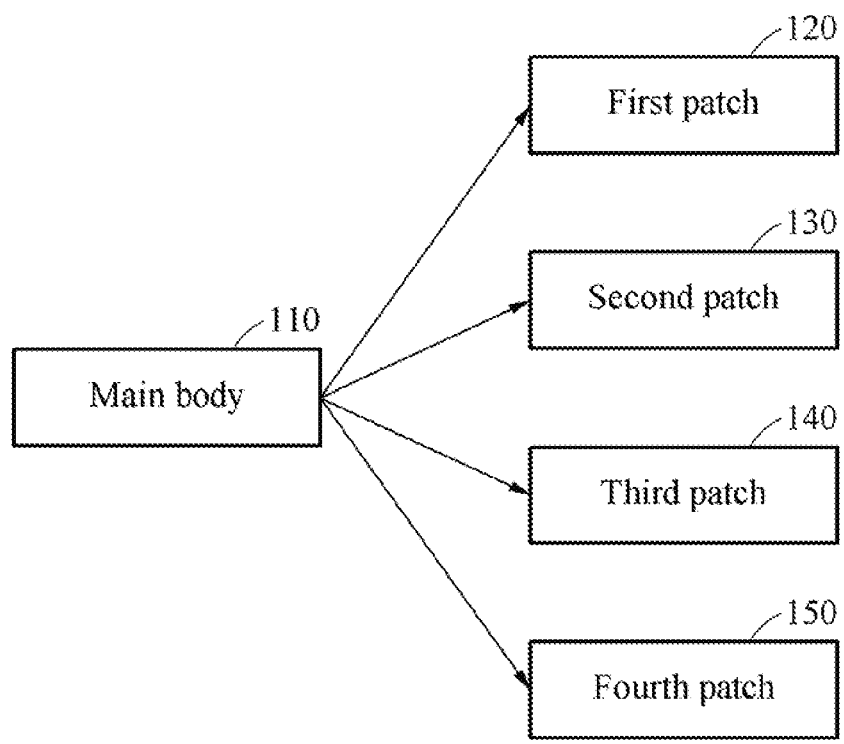
FIG. 1 is a diagram illustrating a deep body spread hyperthermia device according to an example embodiment.

Hereinafter, some example embodiments will be described in detail with reference to the accompanying drawings. Various modifications may be made to the example embodiments. Here, the examples are not construed as limited to the disclosure and should be understood to include all changes, equivalents, and replacements within the idea and the technical scope of the disclosure.

The terminology used herein is for the purpose of describing particular embodiments only and is not intended to be limiting. As used herein, the singular forms are intended to include the plural forms as well, unless the context clearly indicates otherwise. It will be further understood that the terms "comprises" and/or "comprising," when used in this specification, specify the presence of stated features, integers, steps, operations, elements, components or a combination thereof, but do not preclude the presence or addition of one or more other features, integers, steps, operations, elements, components, and/or groups thereof.

Unless otherwise defined herein, all terms used herein including technical or scientific terms have the same meanings as those generally understood by one of ordinary skill in the art. Terms defined in dictionaries generally used should be construed to have meanings matching contextual meanings in the related art and are not to be construed as an ideal or excessively formal meaning unless otherwise defined herein.

When describing the example embodiments with reference to the accompanying drawings, like reference numerals refer to like constituent elements and a repeated description related thereto will be omitted. In the description of example embodiments, detailed description of well-known related structures or functions will be omitted when it is deemed that such description will cause ambiguous interpretation of the present disclosure.

FIG. 1 is a diagram illustrating a deep body spread hyperthermia device according to an example embodiment.

Referring to FIG. 1, a deep body spread hyperthermia device 100 may include a main body 110, a first patch 120, a second patch 130, a third patch 140, and a fourth patch 150.

The main body 110 may generate and output a first signal and a second signal to control the first patch 120, the second patch 130, the third patch 140, and the fourth patch 150. In this example, the second signal may be a control signal having a phase different from a phase of the first signal. Further, the main body 110 may transmit the first signal and the second signal respectively to patches attached to opposing directions based on a body of a user, among the first patch 120, the second patch 130, the third patch 140, and the fourth patch 150.

The first patch 120, the second patch 130, the third patch 140, and the fourth patch 150 may be attached to the skin of the user, and produce hyperthermia in the body of the user by radiating radio waves into the body of the user based on the signals output from the main body 110. For example, the radio waves radiated by the first patch 120, the second patch 130, the third patch 140, and the fourth patch 150 may be microwaves.

Herein, the first patch 120, the second patch 130, the third patch 140, and the fourth patch 150 are defined based on types of signals received from the main body 110 or whether the signals are changed, and may have the same configuration in terms of hardware.

In detail, the first patch 120 may be a patch which receives the first signal from the main body 110 at all times, and the second patch 130 may be a patch which receives the first signal in a first phase and the second signal in a second phase. In addition, the third patch 140 may be a patch which is attached to an opposing direction of the first patch 120 based on the body of the user and receives the second signal at all times, and the fourth patch 150 may be a patch which is attached to an opposing direction of the second patch 130 based on the body of the user and receives the second signal in the first phase and the first signal in the second phase.

Although FIG. 1 illustrates the deep body spread hyperthermia device 100 including 4 patches, the deep body spread hyperthermia device 100 may include $2^{n+1}$ patches in examples. In this example, n may be an integer greater than or equal to "1". For example, the number of patches included in the deep body spread hyperthermia device 100 may increase in the order of 4, 8, 16, 32, and the like.

Further, each of the patches included in the deep body spread hyperthermia device 100 may be classified as one of the first patch 120, the second patch 130, the third patch 140, and the fourth patch 150 based on whether the signal received from the main body 110 is changed depending on a phase, and the received signal.

For example, when the deep body spread hyperthermia device 100 includes 16 patches, the deep body spread hyperthermia device 100 may include 4 patches operating in the same manner as the first patch 120, 4 patches operating in the same manner as the second patch 130, 4 patches operating in the same manner as the third patch 140, and 4 patches operating in the same manner as the fourth patch 150.

The deep body spread hyperthermia device 100 may shift a phase of the first signal and a phase of the second signal to increase a phase difference between the first signal and the second signal over time, thereby moving the position at which hyperthermia is produced by the patches. That is, the deep body spread hyperthermia device 100 may move the position at which hyperthermia is produced by shifting the phase of the first signal and the phase of the second signal, thereby producing hyperthermia in an entire predetermined region of the body of the user to perform hyperthermia therapy.

In this example, hyperthermia may be produced by the patches at a position in a region determined based on the first signal and the second signal respectively transmitted to the patches. There may be a region in which hyperthermia is not produced in the body of the user based on the first signal and the second signal respectively transmitted to the patches.

In this example, the deep body spread hyperthermia device 100 may change types of signals transmitted to the patches such that hyperthermia may be produced in the region in which hyperthermia is not generated by the patches. That is, the deep body spread hyperthermia device 100 may move the region in which hyperthermia is produced by changing the types of the signals transmitted to the patches, thereby producing hyperthermia without any region of the body of the user omitted to perform hyperthermia therapy.

Figure 2:
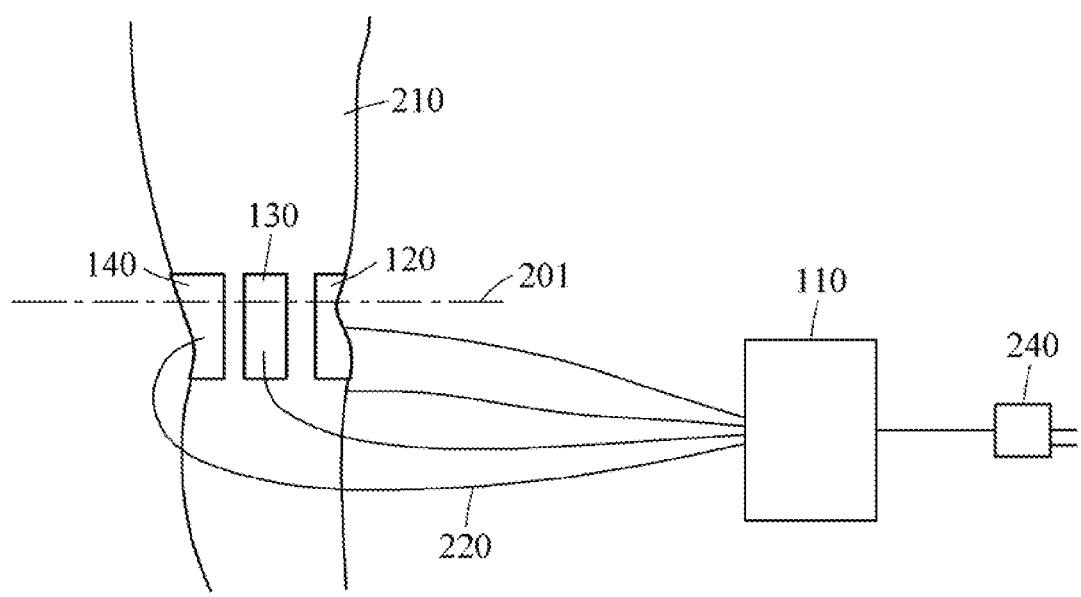
FIG. 2 is a diagram illustrating an example of attaching a deep body spread hyperthermia device to a user according to an example embodiment.

FIG. 2 is a diagram illustrating an example of attaching a deep body spread hyperthermia device to a body 210, for example, a leg, of a user according to an example embodiment. Referring to FIG. 2, the first patch 120, the second patch 130, the third patch 140, and the fourth patch 150 may be attached to the skin around a site of hyperthermia therapy on the leg 210 of the user in a cross section 201. In FIG. 2, although the fourth patch 150 is obscured by the leg 210 of the user, the fourth patch 150 is attached to an opposing side of the second patch 130 based on the leg 210 of the user.

The main body 110 may transmit the first signal or the second signal to the first patch 120, the second patch 130, the third patch 140, and the fourth patch 150 through signal connecting cables 220. Further, the deep body spread hyperthermia device may include a rectifier 240 configured to supply current input from an outside to the main body 110, or supply power to the main body 110 by converting alternating current input from the outside to direct current.

Figure 3:
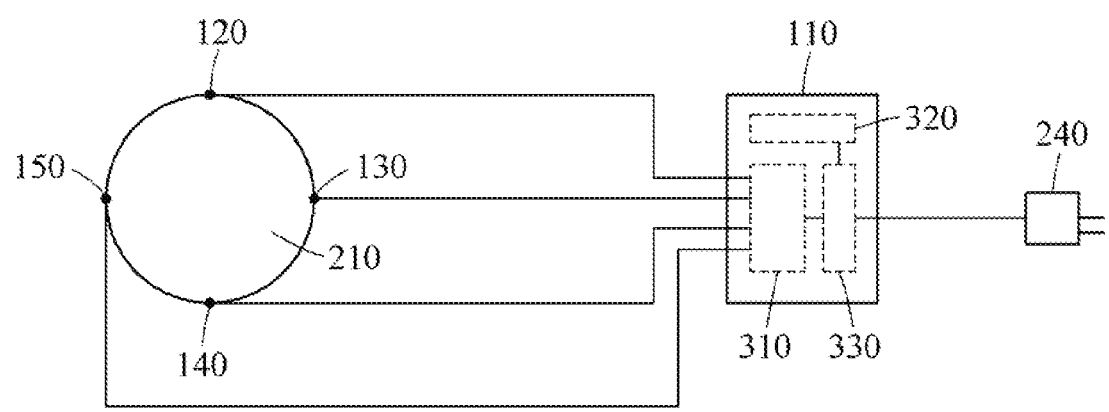
FIG. 3 is a diagram illustrating a structure of a main body of a deep body spread hyperthermia device according to an example embodiment.

FIG. 3 is a diagram illustrating a structure of a main body of a deep body spread hyperthermia device according to an example embodiment.

Referring to FIG. 3, the main body 110 of the deep body spread hyperthermia device may include a signal processor 310, a user input/output unit 320, and an operation processor 330.

The signal processor 310 may generate a control signal, and divide the control signal into a first signal and a second signal.

The user input/output unit 320 may include a visual display configured to display information of the deep body spread hyperthermia device and an input interface configured to receive an instruction from a user. For example, the visual display and the input interface may be integrated into a single device using a touch display configured to receive an instruction from the user through a touch gesture.

The operation processor 330 may supply the power received from the rectifier 240 to the signal processor 310 and the user input/output unit 320. Further, the operation processor 330 may perform an operation based on to a pre-stored program and control the signal processor 310 based on a result of the operation, or display the result of the operation through the user input/output unit 320.

Figure 4:
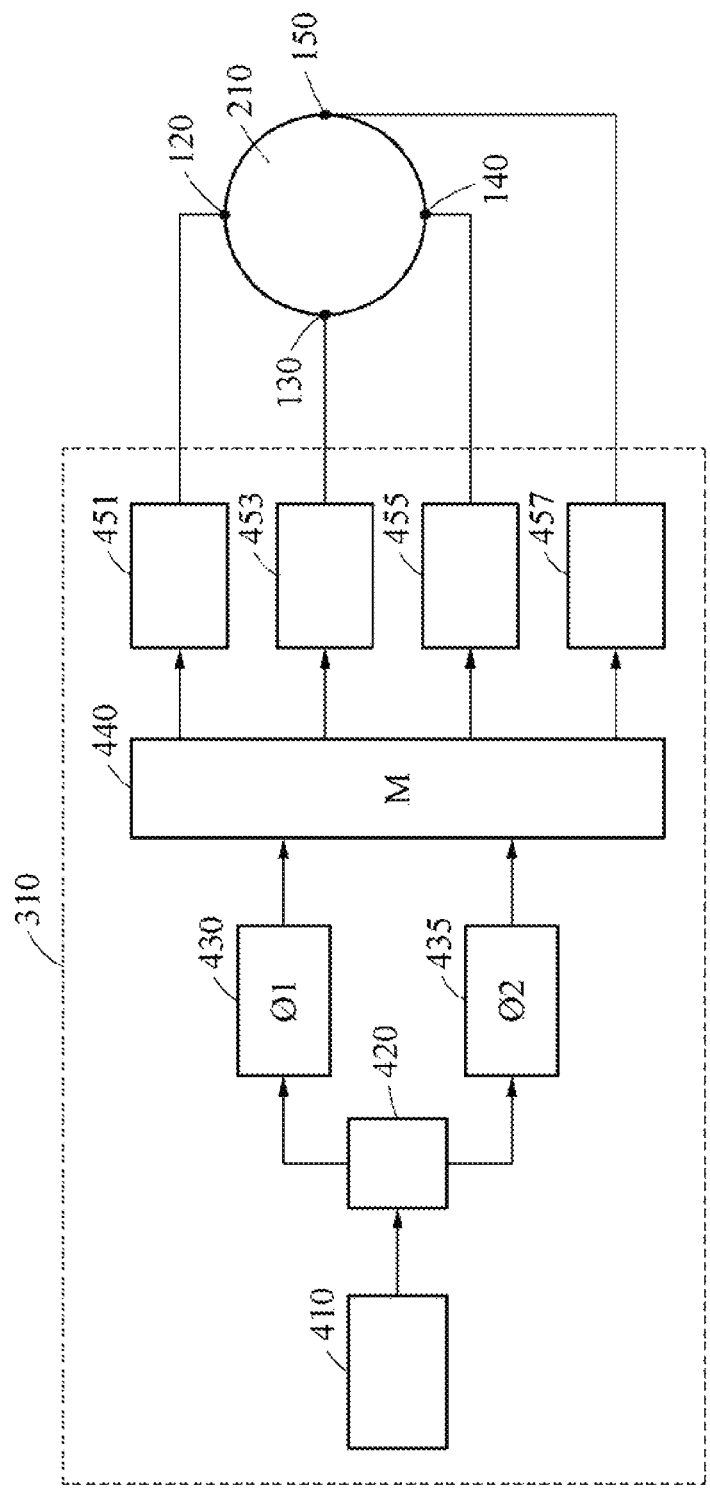
FIG. 4 is a diagram illustrating a structure of a signal processor according to an example embodiment.

FIG. 4 is a diagram illustrating a structure of a signal processor according to an example embodiment.

Referring to FIG. 4, the signal processor 310 may include a signal generator 410, a signal divider 420, a first phase shifter 430, a second phase shifter 435, a phase selection matrix circuit 440, a first high power amplifier 451, a second high power amplifier 453, a third high power amplifier 455, and a fourth high power amplifier 457.

The signal generator 410 may generate and output a control signal to control patches. For example, the control signal may be a microwave signal.

The signal divider 420 may divide the control signal output from the signal generator 410 into two signals and input the signals respectively into the first phase shifter 430 and the second phase shifter 435.

The first phase shifter 430 may generate a first signal by shifting a phase of the control signal divided by the signal divider 420 to φ1.

The second phase shifter 435 may generate a second signal by shifting a phase of the control signal divided by the signal divider 420 to φ2. In this example, the phase φ1 and the phase φ2 may be independent phases.

The phase selection matrix circuit 440 may receive the first signal output from the first phase shifter 430 and the second signal output from the second phase shifter 435. The phase selection matrix circuit 440 may output the first signal and the second signal to the first high power amplifier 451, the second high power amplifier 453, the third high power amplifier 455, and the fourth high power amplifier 457 such that the first signal and the second signal may be transmitted respectively to patches attached to opposing directions, among the patches.

The configuration and the operation of the phase selection matrix circuit 440 for outputting the first signal and the second signal will be described further below with reference to FIGS. 5A and 5B.

The first high power amplifier 451 may amplify the signal received from the phase selection matrix circuit 440 to a high level, and transmit the signal to the first patch 120. The first patch 120 may radiate radio waves into the body 210 of the user based on the signal received from the first high power amplifier 451.

The second high power amplifier 453 may amplify the signal received from the phase selection matrix circuit 440 to a high level, and transmit the signal to the second patch 130. The second patch 130 may radiate radio waves into the body 210 of the user based on the signal received from the second high power amplifier 453.

The third high power amplifier 455 may amplify the signal received from the phase selection matrix circuit 440 to a high level, and transmit the signal to the third patch 140. The third patch 140 may radiate radio waves into the body 210 of the user based on the signal received from the third high power amplifier 455.

The fourth high power amplifier 457 may amplify the signal received from the phase selection matrix circuit 440 to a high level, and transmit the signal to the fourth patch 150. The fourth patch 150 may radiate radio waves into the body 210 of the user based on the signal received from the fourth high power amplifier 457.

Figure 5A:
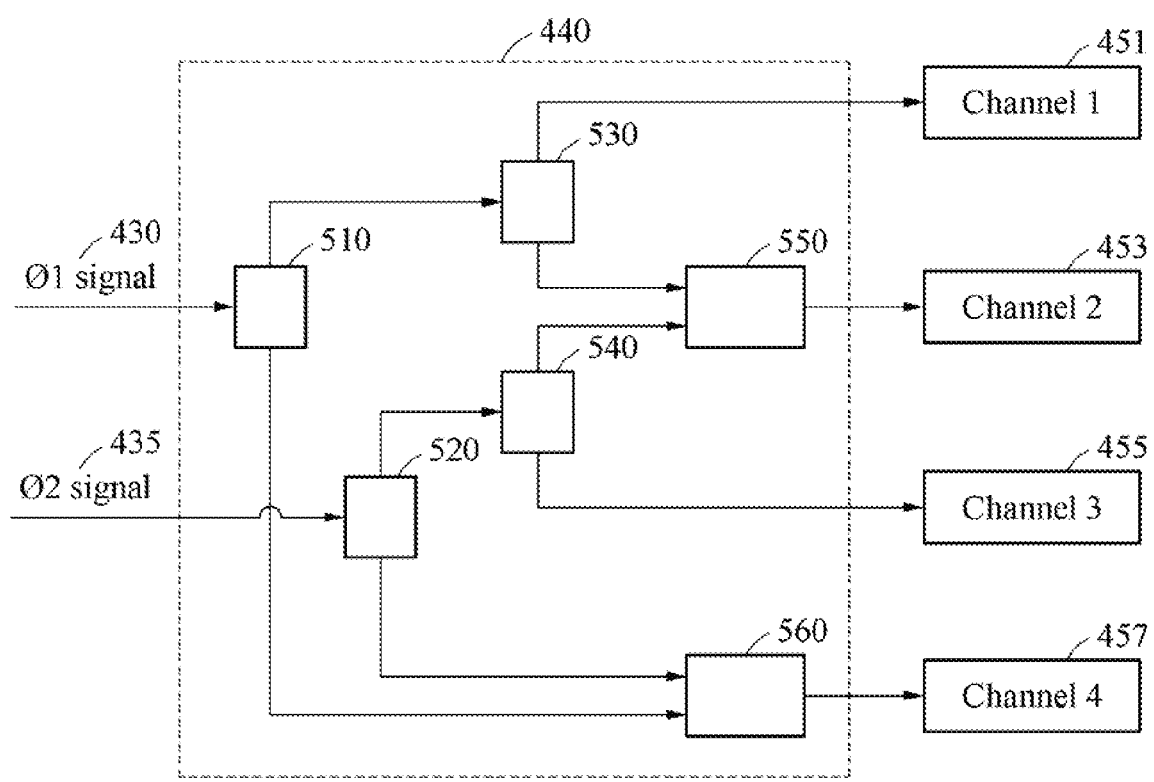

FIGS. 5A and 5B illustrate an example of a phase selection matrix circuit included in a signal processor according to an example embodiment.

Referring to FIGS. 5A and 5B, signals output respectively from the first high power amplifier 451, the second high power amplifier 453, the third high power amplifier 455, and the fourth high power amplifier 457 may be defined as Channel 1 through Channel 4.

The first signal with the phase φ1 input from the first phase shifter 430 into the phase selection matrix circuit 440 may be divided by a first divider 510 and input into a third divider 530 and a second signal selector 560.

Next, the first signal input into the third divider 530 may be divided by the third divider 530 and input into the first high power amplifier 451 and a first signal selector 550. That is, the first signal with the phase φ1 may be output to Channel 1 to be transmitted to the first patch 120 through the first high power amplifier 451.

Further, the second signal with the phase φ2 input from the second phase shifter 435 into the phase selection matrix circuit 440 may be divided by a second divider 520 and input into a fourth divider 540 and the second signal selector 560.

Next, the second signal input into the fourth divider 540 may be divided by the fourth divider 540 and input into the first signal selector 550 and the third high power amplifier 455. That is, the second signal with the phase φ2 may be output to Channel 3 to be transmitted to the third patch 140 through the third high power amplifier 455.

In this example, the first signal selector 550 may receive the first signal divided by the third divider 530 and the second signal divided by the fourth divider 540. The first signal selector 550 may select one of the first signal and the second signal based on whether a current phase of the signal processor 440 is a first phase or a second phase, and output the selected signal to the second high power amplifier 453.

Further, the second signal selector 560 may receive the first signal divided by the first divider 510 and the second signal divided by the second divider 520. The second signal selector 560 may select one of the first signal and the second signal based on whether the current phase of the signal processor 440 is the first phase or the second phase, and output the selected signal to the fourth high power amplifier 457.

In this example, the second signal selector 560 and the first signal selector 550 may select different signals. For example, when the first signal selector 550 outputs the first signal, the second signal selector 560 may output the second signal.

For example, per-channel signals may be defined as shown in a table of FIG. 5B. When the current phase is the first phase, an internal switch may be controlled to connect the first signal selector 550 to the third divider 530. In addition, an internal switch may be controlled to connect the second signal selector 560 to the second divider 520.

In this example, the first signal selector 550 may output the first signal received from the third divider 530 to Channel 2. Further, the second signal selector 560 may output the second signal received from the second divider 520 to Channel 4.

Conversely, when the current phase is the second phase, the internal switch may be controlled to connect the first signal selector 550 to the fourth divider 540. In addition, the internal switch may be controlled to connect the second signal selector 560 to the first divider 510.

In this example, the first signal selector 550 may output the second signal received from the fourth divider 540 to Channel 2. Further, the second signal selector 560 may output the first signal received from the first divider 510 to Channel 4.

In this example, the second patch 130 corresponding to Channel 2 and the fourth patch 150 corresponding to Channel 4 may be attached to opposing directions based on the body of the user, as shown in FIGS. 3 and 4. Thus, even when signals input into the second patch 130 and the fourth patch 150 are switched, the condition that patches attached to opposing directions should have different phases may be maintained.

Figure 6:
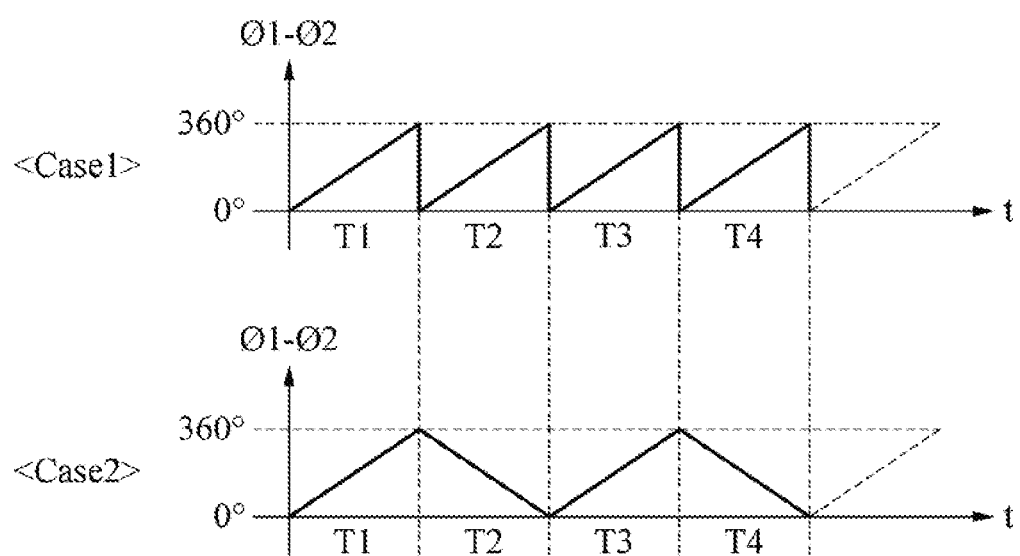
FIG. 6 illustrates an example of a change in phase difference between a first signal and a second signal over time according to an example embodiment.

FIG. 6 illustrates an example of a change in phase difference between a first signal and a second signal over time according to an example embodiment.

A deep body spread hyperthermia device may shift a phase of a first signal and a phase of a second signal to increase a phase difference between the first signal and the second signal over time, thereby moving a position at which hyperthermia is produced by patches in a body of a user.

For example, when a signal processor increases the phase difference between the first signal and the second signal 360 degrees at time intervals, a change in the phase difference between the first signal and the second signal for each time interval may be as shown in Case 1 of FIG. 6. The phase difference between the first signal and the second signal increased to 360 degrees at each interval may be substantially equal to 0 degrees. Thus, when the signal processor increases the phase difference between the first signal and the second signal 360 degrees at each time interval, the phase difference between the first signal and the second signal may be increased repetitively from 0 degrees to 360 degrees at time intervals as shown in Case 1 of FIG. 6.

In another example, when the signal processor repeats increasing and decreasing the phase difference between the first signal and the second signal at time intervals, a change in the phase difference between the first signal and the second signal for each time interval may be as shown in Case 2 of FIG. 6. In detail, the signal processor may repeat increasing the phase difference between the first signal and the second signal from 0 degrees to 360 degrees at a first time interval, and decreasing the phase difference between the first signal and the second signal from 360 degrees to 0 degrees at a second time interval following the first time interval.

In this example, the first time interval may be an odd-numbered interval such as T1, T3, or T5, and the second time interval may be an even-numbered interval such as T2, T4, or T6.

In some examples, the signal processor may decrease the phase difference between the first signal and the second signal from 360 degrees to 0 degrees at the first time interval, and increase the phase difference between the first signal and the second signal from 0 degrees to 360 degrees at the second time interval.

Figure 7A:
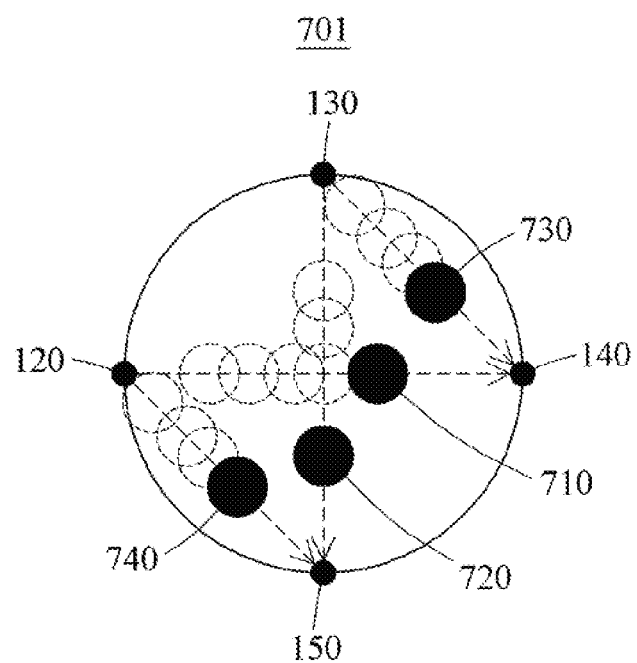
FIGS. 7A and 7B illustrate examples of moving a hyperthermia producing position according to an example embodiment.
Figure 7B:
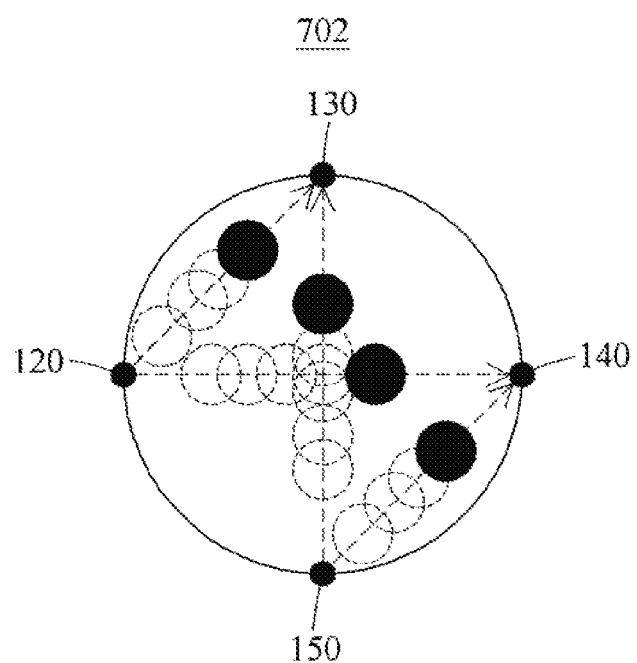

FIGS. 7A and 7B illustrate examples of moving a hyperthermia producing position according to an example embodiment.

When a current phase is a first phase, and a phase difference between a first signal and a second signal changes as shown in Case 1 of FIG. 6, a position 740 of hyperthermia produced between the first patch 120 and the fourth patch 150, a position 720 of hyperthermia produced between the second patch 130 and the fourth patch 150, a position 730 of hyperthermia produced between the second patch 130 and the third patch 140, and a position 710 of hyperthermia produced between the first patch 120 and the third patch 140 may change as shown in Case 1 of FIG. 7A.

Figure 8A:
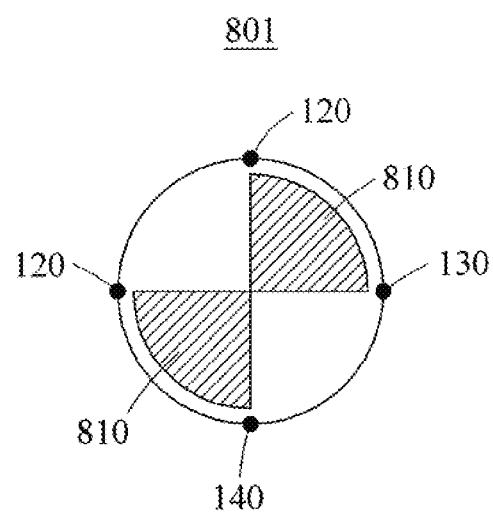
FIGS. 8A through 8C illustrate examples of hyperthermia regions generated according to an example embodiment.

In this example, in response to the changes in the position 710 of hyperthermia through the position 740 of hyperthermia, hyperthermia may diffuse into regions 810 to which the positions of hyperthermia are moved, as shown in Case 1 of FIG. 8A.

When the current phase is a second phase, and the phase difference between the first signal and the second signal changes as shown in Case 1 of FIG. 6, a position 735 of hyperthermia produced between the first patch 120 and the second patch 130, a position 725 of hyperthermia produced between the second patch 130 and the fourth patch 150, a position 715 of hyperthermia produced between the first patch 120 and the third patch 140, and a position 745 of hyperthermia produced between the third patch 140 and the fourth patch 150 may change as shown in Case 2 of FIG. 7B.

Figure 8B:
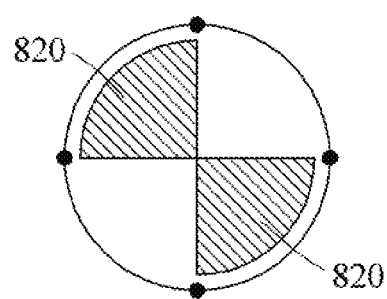

In this example, in response to the changes in the position 715 of hyperthermia through the position 745 of hyperthermia, hyperthermia may diffuse into regions 820 to which the positions of hyperthermia are moved, as shown in Case 2 of FIG. 8B.

Figure 8C:
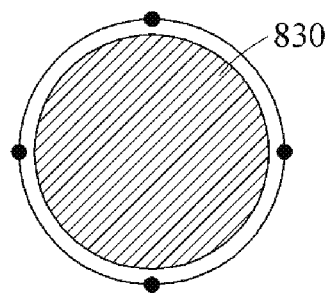

Comparing Case 1 of FIG. 8A and Case 2 of FIG. 8B, hyperthermia may diffuse into different regions. Thus, the signal processor may periodically switch the first phase and the second phase such that hyperthermia may diffuse into the entire region 830 in the body of the user as shown in Case 3 of FIG. 8C.

Figure 9A:
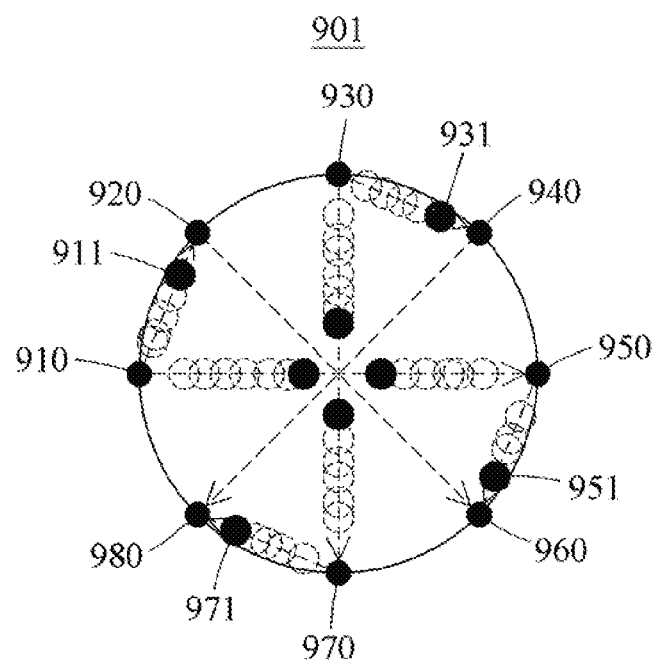
FIGS. 9A and 9B illustrate examples of moving a hyperthermia producing position according to an example embodiment.
Figure 9B:
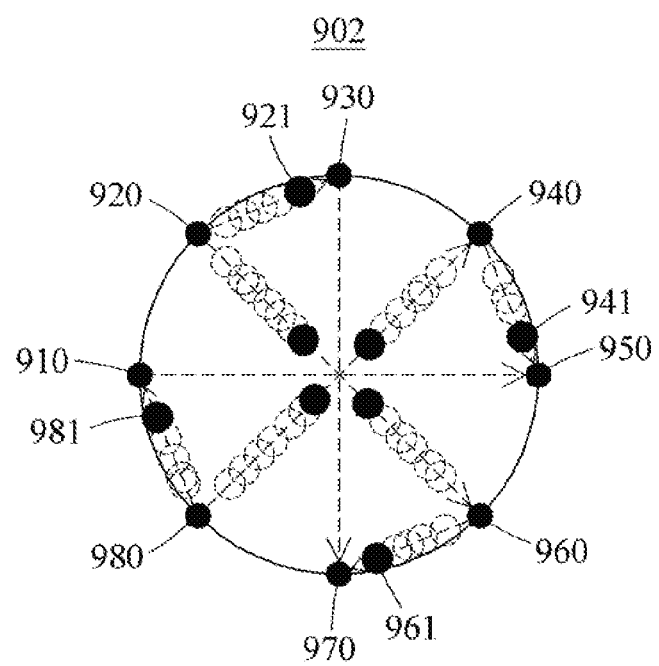

FIGS. 9A and 9B illustrate examples of moving a hyperthermia producing position using a deep body spread hyperthermia device including 8 patches according to an example embodiment. In this example, the deep body spread hyperthermia device may include a first patch 910, a second patch 920, a third patch 930, a fourth patch 940, a fifth patch 950, a sixth patch 960, a seventh patch 970, and an eighth patch 980.

When a current phase is a first phase, and a phase difference between a first signal and a second signal changes as shown in Case 1 of FIG. 6, a position 911 of hyperthermia produced between the first patch 910 and the second patch 920, a position 912 of hyperthermia produced between the first patch 910 and the fifth patch 950, a position 931 of hyperthermia produced between the third patch 930 and the fourth patch 940, a position 932 of hyperthermia produced between the third patch 930 and the seventh patch 970, a position 951 of hyperthermia produced between the fifth patch 950 and the sixth patch 960, a position 952 of hyperthermia produced between the fifth patch 950 and the first patch 910, a position 971 of hyperthermia produced between the seventh patch 970 and the eighth patch 980, and a position 972 of hyperthermia produced between the seventh patch 970 and the third patch 930 may change as shown in Case 1 of FIG. 9A.

Figure 10A:
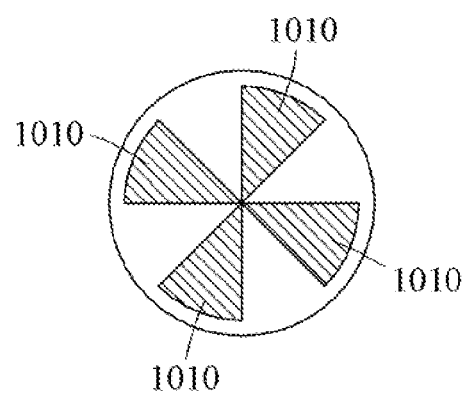
FIGS. 10A through 10C illustrate examples of hyperthermia regions generated according to an example embodiment.

In this example, in response to the changes in the position 910 of hyperthermia through the position 972 of hyperthermia, hyperthermia may diffuse into regions 1010 to which the positions of hyperthermia are moved, as shown in Case 1 of FIG. 10A.

When the current phase is a second phase, and the phase difference between the first signal and the second signal changes as shown in Case 1 of FIG. 6, a position 981 of hyperthermia produced between the first patch 910 and the eighth patch 980, a position 982 of hyperthermia produced between the eighth patch 980 and the fourth patch 940, a position 921 of hyperthermia produced between the second patch 920 and the third patch 930, a position 922 of hyperthermia produced between the second patch 920 and the sixth patch 960, a position 941 of hyperthermia produced between the fourth patch 940 and the fifth patch 950, a position 942 of hyperthermia produced between the fourth patch 940 and the eighth patch 980, a position 961 of hyperthermia produced between the sixth patch 960 and the seventh patch 970, and a position 962 of hyperthermia produced between the sixth patch 960 and the second patch 920 may change as shown in Case 2 of FIG. 9B.

Figure 10B:
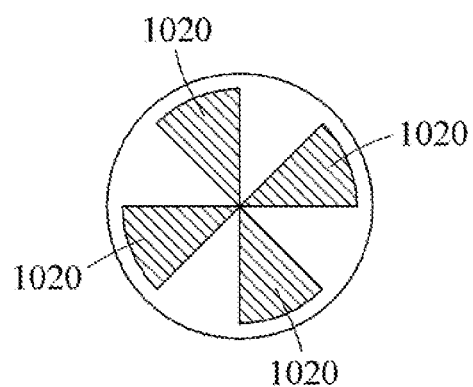

In this example, in response to the changes in the position 921 of hyperthermia through the position 982 of hyperthermia, hyperthermia may diffuse into regions 1020 to which the positions of hyperthermia are moved, as shown in Case 2 of FIG. 10B.

Figure 10C:
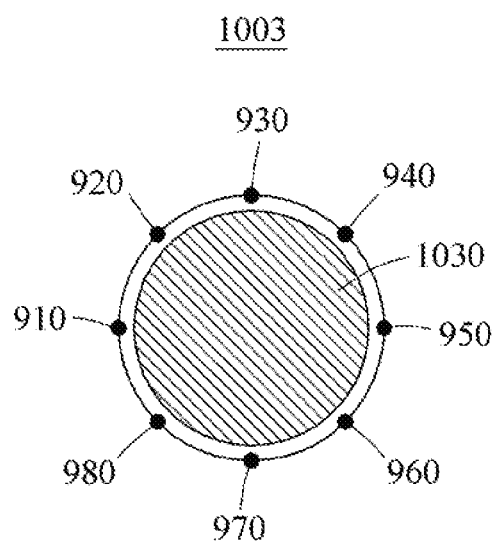

Comparing Case 1 of FIG. 10A and Case 2 of FIG. 10B, hyperthermia may diffuse into different regions. Thus, the signal processor may periodically switch the first phase and the second phase such that hyperthermia may diffuse into the entire region 1030 in the body of the user as shown in Case 3 of FIG. 10C.

FIG. 11 is a flowchart illustrating a deep body spread method according to an example embodiment.

Referring to FIG. 11, in operation 1110, the signal processor 310 may generate a control signal to control patches attached to the skin of a user.

In operation 1120, the signal processor 310 may divide the control signal generated in operation 1110 into a first signal and a second signal having a phase different and independent from a phase of the first signal.

In operation 1130, the signal processor 310 may shift a phase of the first signal and a phase of the second signal to increase a phase difference between the first signal and the second signal over time. In this example, the signal processor 310 may increase the phase difference between the first signal and the second signal 360 degrees at time intervals. Further, the signal processor 310 may increase the phase difference between the first signal and the second signal from 0 degrees to 360 degrees at a first time interval, and decrease the phase difference between the first signal and the second signal from 360 degrees to 0 degrees at a second time interval following the first time interval.

In operation 1140, the signal processor 310 may transmit the first signal and the second signal to patches attached to different positions, among the patches. In this example, the signal processor 310 may transmit the phase-shifted first signal and the phase-shifted second signal to patches attached to different positions, among the patches. In addition, the signal processor 310 may change signals to be transmitted to the patches from the first signal to the second signal or from the second signal to the first signal to change a position of hyperthermia to be produced in a body of the user.

In this example, the signal processor 310 may transmit the first signal and the second signal respectively to the first patch 120 and the third patch 140, and the first signal or the second signal to the second patch 130 and the fourth patch 150 depending on a phase. For example, the signal processor 310 may transmit the first signal to the second patch 130 and the second signal to the fourth patch 150 in the first phase. Further, the signal processor 310 may transmit the second signal to the second patch 130 and the first signal to the fourth patch 150 in the second phase.

In operation 1150, the patches may produce hyperthermia in the body of the user by radiating radio waves into the body of the user based on the first signal or the second signal received by each of the patches.

According to example embodiments, it is possible to move a position at which hyperthermia is produced by patches, by shifting a phase of a first signal and a phase of a second signal to increase a phase difference between the first signal and the second signal over time. That is, the position at which hyperthermia is produced may be moved by shifting the phase of the first signal and the phase of the second signal, whereby hyperthermia may be produced in the entire region of a body of a user to perform hyperthermia therapy.

According to example embodiments, it is possible to produce hyperthermia in a region in which hyperthermia is not produced by patches, by changing types of signals to be transmitted to the patches. That is, the region in which hyperthermia is produced may be moved by changing the types of the signals to be transmitted to the patches, whereby hyperthermia may be produced without any region of a body of a user omitted to perform hyperthermia therapy.

The components described in the example embodiments may be implemented by hardware components including, for example, at least one digital signal processor (DSP), a processor, a controller, an application-specific integrated circuit (ASIC), a programmable logic element, such as a field programmable gate array (FPGA), other electronic devices, or combinations thereof. At least some of the functions or the processes described in the example embodiments may be implemented by software, and the software may be recorded on a recording medium. The components, the functions, and the processes described in the example embodiments may be implemented by a combination of hardware and software.

The methods according to the above-described example embodiments may be recorded in non-transitory computer-readable media including program instructions to implement various operations of the above-described example embodiments. The media may also include, alone or in combination with the program instructions, data files, data structures, and the like. The program instructions recorded on the media may be those specially designed and constructed for the purposes of example embodiments, or they may be of the kind well-known and available to those having skill in the computer software arts. Examples of non-transitory computer-readable media include magnetic media such as hard disks, floppy disks, and magnetic tape; optical media such as CD-ROM discs, DVDs, and/or Blue-ray discs; magneto-optical media such as optical discs; and hardware devices that are specially configured to store and perform program instructions, such as read-only memory (ROM), random access memory (RAM), flash memory (e.g., USB flash drives, memory cards, memory sticks, etc.), and the like. Examples of program instructions include both machine code, such as produced by a compiler, and files containing higher level code that may be executed by the computer using an interpreter. The above-described devices may be configured to act as one or more software modules in order to perform the operations of the above-described example embodiments, or vice versa.

The software may include a computer program, a piece of code, an instruction, or some combination thereof, to independently or collectively instruct or configure the processing device to operate as desired. Software and data may be embodied permanently or temporarily in any type of machine, component, physical or virtual equipment, computer storage medium or device, or in a propagated signal wave capable of providing instructions or data to or being interpreted by the processing device. The software also may be distributed over network coupled computer systems so that the software is stored and executed in a distributed fashion. The software and data may be stored by one or more non-transitory computer readable recording mediums.

A number of example embodiments have been described above. Nevertheless, it should be understood that various modifications may be made to these example embodiments. For example, suitable results may be achieved if the described techniques are performed in a different order and/or if components in a described system, architecture, device, or circuit are combined in a different manner and/or replaced or supplemented by other components or their equivalents. Accordingly, other implementations are within the scope of the following claims.

What is claimed is:

1. An operating method of a deep body spread hyperthermia device, the operating method comprising:
   generating a control signal to control patches attached to the skin of a user;
   dividing the control signal into a first signal and a second signal having a phase different from a phase of the first signal;
   transmitting the first signal and the second signal respectively to patches attached to opposing directions based on a body of a user, among the patches;
   producing hyperthermia in a body of the user by radiating radio waves based on the first signal or the second signal received by each of the patches; and
   shifting a phase of the first signal and a phase of the second signal to increase a phase difference between the first signal and the second signal over time, wherein the transmitting comprises transmitting the phase-shifted first signal and the phase-shifted second signal to patches attached to different positions, among the patches.

2. The operating method of claim 1, wherein the shifting comprises increasing the phase difference between the first signal and the second signal 360 degrees at time intervals.

3. The operating method of claim 1, wherein the shifting comprises repeating increasing the phase difference between the first signal and the second signal from 0 degrees to 360 degrees at a first time interval, and decreasing the phase difference between the first signal and the second signal from 360 degrees to 0 degrees at a second time interval following the first time interval.

4. The operating method of claim 1, wherein the transmitting comprises changing signals to be transmitted to the patches from the first signal to the second signal or from the second signal to the first signal to change a position of hyperthermia to be produced in the body of the user.

5. The operating method of claim 1, wherein the patches comprise a first patch, a second patch, a third patch attached to an opposing direction of the first patch, and a fourth patch attached to an opposing direction of the second patch based on the body of the user, and
the transmitting comprises:
transmitting the first signal and the second signal to the first patch and the third patch, respectively; and
transmitting the first signal or the second signal to the second patch and the fourth patch depending on a phase.

6. The operating method of claim 5, wherein the transmitting comprises:
transmitting the first signal to the second patch and the second signal to the fourth patch in a first phase; and
transmitting the second signal to the second patch and the first signal to the fourth patch in a second phase.

7. A deep body spread hyperthermia device, comprising:
a plurality of patches to be attached to the skin of a user to produce hyperthermia in a body of the user by radiating radio waves into the body of the user; and
a signal processor configured to generate a first signal and a second signal having a phase different from a phase of the first signal to control the patches to radiate the radio waves, and transmit the first signal and the second signal to the patches,
wherein the signal processor is configured to transmit the first signal and the second signal respectively to patches attached to opposing directions based on a body of a user, among the patches, and
wherein the signal processor is configured to shift a phase of the first signal and a phase of the second signal to increase a phase difference between the first signal and the second signal over time.

8. The deep body spread hyperthermia device of claim 7, wherein the signal processor is configured to increase the phase difference between the first signal and the second signal 360 degrees at time intervals.

9. The deep body spread hyperthermia device of claim 7, wherein the signal processor is configured to repeat increasing the phase difference between the first signal and the second signal from 0 degrees to 360 degrees at a first time interval, and decreasing the phase difference between the first signal and the second signal from 360 degrees to 0 degrees at a second time interval following the first time interval.

10. The deep body spread hyperthermia device of claim 7, wherein the signal processor is configured to change signals to be transmitted to the patches from the first signal to the second signal or from the second signal to the first signal to change a position of hyperthermia to be produced in the body of the user.

11. The deep body spread hyperthermia device of claim 7, wherein the patches comprise:
a first patch configured to receive the first signal at all times;
a second patch configured to receive the first signal in a first phase and receive the second signal in a second phase;
a third patch to be attached to an opposing direction of the first patch based on the body of the user, the third patch configured to receive the second signal at all times; and
a fourth patch to be attached to an opposing direction of the second patch based on the body of the user, the fourth patch configured to receive the second signal in the first phase and receive the first signal in the second phase.

12. The deep body spread hyperthermia device of claim 11, wherein the signal processor is configured to:
transmit the first signal to the second patch and the second signal to the fourth patch in the first phase, and
transmit the second signal to the second patch and the first signal to the fourth patch in the second phase.

* * * * *